United States Patent
Zhang

(10) Patent No.: US 11,468,989 B2
(45) Date of Patent: Oct. 11, 2022

(54) MACHINE-AIDED DIALOG SYSTEM AND MEDICAL CONDITION INQUIRY APPARATUS AND METHOD

(71) Applicant: BOE TECHNOLOGY GROUP CO., LTD., Beijing (CN)

(72) Inventor: Zhenzhong Zhang, Beijing (CN)

(73) Assignee: Beijing BOE Technology Development Co., Ltd., Beijing (CN)

(*) Notice: Subject to any disclaimer, the term of this patent is extended or adjusted under 35 U.S.C. 154(b) by 189 days.

(21) Appl. No.: 16/631,824

(22) PCT Filed: Feb. 20, 2019

(86) PCT No.: PCT/CN2019/075582
§ 371 (c)(1),
(2) Date: Jan. 16, 2020

(87) PCT Pub. No.: WO2020/057052
PCT Pub. Date: Mar. 26, 2020

(65) Prior Publication Data
US 2021/0241906 A1      Aug. 5, 2021

(30) Foreign Application Priority Data

Sep. 19, 2018    (CN) .......................... 201811099001.0

(51) Int. Cl.
*G16H 20/40*      (2018.01)
*G16H 50/20*      (2018.01)
(Continued)

(52) U.S. Cl.
CPC ......... *G16H 50/20* (2018.01); *G06F 16/2379* (2019.01); *G06F 40/30* (2020.01);
(Continued)

(58) Field of Classification Search
CPC .................................................... G16H 50/20
See application file for complete search history.

(56) References Cited

U.S. PATENT DOCUMENTS 11,128,579 B2 * 9/2021 Magliozzi ............ G06Q 10/107
2017/0308531 A1   10/2017 Ma et al.

FOREIGN PATENT DOCUMENTS

CN    104573028 A    4/2015
CN    107247868 A    10/2017
(Continued)

OTHER PUBLICATIONS

"Tutorial on Estimation and Multivariate Gaussians", Toyota Technical Institute, Oct. 2015 (Year: 2015).*
(Continued)

*Primary Examiner* — Aryan E Weisenfeld
(74) *Attorney, Agent, or Firm* — Arch & Lake LLP

(57) ABSTRACT

A machine-aided dialog system as well as a medical condition inquiry method and apparatus employing the machine aided dialog system are disclosed. There is provided a machine-aided dialog system, comprising: a semantic framework for providing a dialog theme; a knowledge database for storing semantic knowledge, the semantic knowledge comprising at least one group of content-related language expressions manners; and a dialog manager for managing a dialog according to the dialog theme provided by the semantic framework, wherein the managing a the dialog comprises: generating a question expression of the dialog theme based on the semantic knowledge acquired from the knowledge database; and ending the dialog theme once upon determining that the dialog theme is completed in response to a dialog ending condition.

14 Claims, 3 Drawing Sheets

(51) Int. Cl.
  *G16H 70/60* (2018.01)
  *G16H 15/00* (2018.01)
  *G16H 10/20* (2018.01)
  *G06F 16/23* (2019.01)
  *G06F 40/30* (2020.01)

(52) U.S. Cl.
  CPC .............. *G16H 10/20* (2018.01); *G16H 15/00* (2018.01); *G16H 70/60* (2018.01)

(56) References Cited

FOREIGN PATENT DOCUMENTS

| CN | 107358052 A | 11/2017 |
|---|---|---|
| CN | 107545148 A | 5/2018 |

OTHER PUBLICATIONS

"Text Analysis 101," Mike Waldron, Apr. 30, 2015 (Year: 2015).*
Haralambous, Thematically Reinforced Explicit Semantic Analysis, https://arxiv.org/pdf/1405.4364.pdf, (Year: 2014).*
Oracle, https://docs.oracle.com/en/database/oracle/machine-learning/oml4py/1/mlpug/explicit-semantic-analysis.html (Year: 2021).*
International Search Report Issued in Application No. PCT/CN2019/075582, dated Jun. 19, 2019, (9p).
First Office Action issued in Indian Patent Application No. 202047022146 dated Aug. 13, 2021 with partial machine translation, (4p).
First Office Action issued in Korean Patent Application No. 2020-7015553 dated Nov. 24, 2021 with English translation, (17p).

* cited by examiner

MACHINE-AIDED DIALOG SYSTEM AND MEDICAL CONDITION INQUIRY APPARATUS AND METHOD

CROSS-REFERENCE TO RELATED APPLICATIONS

This application is based upon and claims the priority of PCT patent application No. PCT/CN2019/075582 filed on Feb. 20, 2019 which claims the priority of Chinese Patent Application No. 201811099001.0 filed on Sep. 19, 2018, the entire content of all of which is hereby incorporated by reference herein for all purposes.

TECHNICAL FIELD

The disclosure relates to the field of artificial intelligence, and in particular to a machine-aided dialog system, and a medical condition inquiry method and apparatus.

BACKGROUND

Man-machine dialog has wide applications to education, medicine, statistics and other areas.

For example, in the medical field, a great number of patients see doctors, causing hospitals overloaded. Doctors cannot diagnose patients timely, and this gives the patients the impression of low efficiency. During a diagnosis, a patient hopes to get a rapid treatment to relieve the uncomfortable symptom in the body, while the doctor needs to know the patient's condition very well so as to provide a reasonable solution for treatment. In this case, the doctor needs to spend a lot of time communicating with the patient to guide the patient to describe his or her illness.

In the process when the doctor communicates with the patient, the doctor can communicate with one patient only, while other patients need to wait outside in line.

SUMMARY

According to one aspect of the disclosure, there is provided a machine-aided dialog system, comprising: a semantic framework for providing a dialog theme; a knowledge database for storing semantic knowledge, the semantic knowledge comprising at least one group of content-related expressions; and a dialog manager for managing a dialog according to the dialog theme provided by the semantic framework, wherein managing the dialog comprises: generating a question expression of the dialog theme based on the semantic knowledge acquired from the knowledge database; and ending the dialog theme upon determining that the dialog theme is completed in response to a dialog ending condition.

In some embodiments, managing the dialog further comprises: according to a received response expression, extracting a keyword from the received response expression based on a semantic context and/or syntactic structure in the semantic knowledge; and generating one or more question expressions according to the keyword in the response expression and a preset expression generation template.

Optionally, the dialog manager comprises a mapping sub-unit for mapping a term in a response expression into a corresponding expression of the semantic knowledge, the mapping sub-unit comprising: a term vector calculator for calculating a term vector of each term in a term set, wherein both a set of predetermined expressions of the sematic knowledge and a set of terms in the response expression are proper subsets of the term set; a similarity calculator for respectively calculating similarities between a term in the response expression and each expression in the set of predetermined expressions according to a term vector of the term and term vectors of all expressions in the set of predetermined expressions; and a replacer for replacing the term in the response expression with the corresponding expression of the semantic knowledge in response to the condition that the calculated similarity meets a threshold condition.

Optionally, the term vector calculator is further configured to indicate each term in the term set as a multi-dimensional Gaussian distribution and take a mean value of the multi-dimensional Gaussian distribution as a term vector of the each term; and the term vector calculator calculates the term vector of each term in the term set in a following manner: it is assumed that each term w in the term set represents a multi-dimensional Gaussian distribution $f(w)$–$N(\mu_w, \Sigma_w)$, where $\mu_w$ and $\Sigma_w$ respectively represent a mean value and a covariance of the multi-dimensional Gaussian distribution of the term w, and $\Sigma_w$ is a diagonal matrix, $$L(w, c_p, c_n) = \max(0, 1 - S(w, c_p) + S(w, c_n)) \quad (1)$$

where cp and cn both are elements in the term set, cp is a term in context of the term w in all response expressions received by the machine-aided dialog system, cn is a term not appearing in the contexts of the term w in any response expressions received by the machine-aided dialog system, and function S(.,.) represents a similarity calculation function; and for given terms w1 and w2, a similarity between w1 and w2 is calculated as follows:

$$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx \quad (2)$$

$$= \frac{1}{2} \{ tr(\Sigma_{w_1}^{-1} \Sigma_{w_2}) + (u_{w_1} - u_{w_2})^T \Sigma_{w_1}^{-1} (u_{w_1} - u_{w_2}) -$$

$$\log \frac{\det(\Sigma_{w_2})}{\det(\Sigma_{w_1})} - d \}$$

where tr( ) represents calculating a trace of the matrix, $\Sigma^{-1}$ represents an inversion of the matrix, det represents calculating a value of a determinant, and d represents a constant irrelevant to $\mu$ and $\Sigma$;

the mean value $\mu_w$ of the Gaussian distribution of the term w, the mean value $\mu_{cp}$ of the Gaussian distribution of cp, and the mean value $\mu_{cn}$ of the Gaussian distribution of cn when L is minimum are calculated by substituting the formula (2) to the formula (1), and the mean values are respectively taken as term vectors of the term w, cp and cn; and the above operations are repeated till the term vectors of all terms in the term set are obtained.

Optionally, the term vector calculator is further configured to decompose a term-term matrix, at least partially map a term to a potential semantic space based on an Explicit Semantic Analysis (ESA) to obtain a vector of the term in the potential semantic space and take the vector as a term vector of the term; and the term vector calculator calculates the term vector of each term in the term set in a following manner:

$$M \approx P^T W \quad (3)$$

$$\min_{P,W} \sum_{i=1}^{n}\sum_{j=1}^{m}(M_{i,j} - P_i^T W_j)^2 + \alpha \sum_{i=1}^{n}\sum_{f=1}^{n} E_{i,f}\|P_i - P_f\|_F^2 + \lambda(\|P\|_F^2 + \|W\|_F^2) \quad (4)$$

where V={v1, v2, . . . , vm} represents the term set, vi and vj (1≤i, j≤m) each represents a single term, M∈Rm×m represents the term-term matrix, Mi,j is a Term Frequency-Inverse Document Frequency (tf–idf) weight of the term vj in the term vi, Ei,j is a similarity between the terms vi and vj, $\|\cdot\|_F^2$ is a Frobenius norm, a and A, are preset non-negative parameters, P∈Rk×m, W∈Rk×m, and R is a real number; and P is calculated under a condition in which the formula (4) is minimum according to the formula (3) and the formula (4), and a term vector $P_i$ of the term vi and a term vector $P_j$ of the term vj are obtained.

Optionally, the condition that the similarity meets the threshold condition comprises: a cosine similarity between the term vector of the term in the response expression and a term vector of the corresponding expression of the semantic knowledge is greater than or equal to a predetermined threshold.

According to another aspect of the disclosure, there is provided a medical condition inquiry apparatus, comprising: a user interactive interface for providing a dialog with a patient, including inquiring a patient's health status and receiving a response from the patient; a semantic analyzer, for extracting medical information of the patient based on the response from the patient, wherein the response from the patient is a first expression in a first expression category; a medical knowledge database storing a second expression of a medical condition corresponding to the medical information, wherein the second expression is in a second expression category; and a report generator, for generating a medical condition inquiry report having the medical information with the second expression.

In some embodiments, it further comprises an inquiry framework for storing a dialog theme having a plurality of inquiry subjects; and a dialog manager for managing the dialog with the patient based on the inquiry subjects of the dialog theme.

Optionally, the dialog manager is configured to generate a first inquiry question, with expressions in the first expression category, relating to a first inquiry subject.

Optionally, the dialog manager is further configured to detect responsiveness of the first inquiry subject by the response from the patient.

Optionally, the dialog manager, upon detection of responsiveness to the first inquiry subject, is further configured to generate a second inquiry question, with expressions in the first expression category, relating to a second inquiry subject.

Optionally, the dialog manager, upon detection of responsiveness to all inquiry subjects of the dialog theme, is configured to end the dialog with the patient.

Optionally, the first expression category includes expressions in plain languages and the second expression category includes expressions in academic language.

According to a further aspect of the disclosure, there is provided a method of medical condition inquiry, comprising: providing a dialog with a patient from a user interactive interface, including inquiring a patient's health status and receiving a response from the patient; extracting medical information of the patient based on the response from the patient, wherein the response from the patient is a first expression in a first expression category; accessing a medical knowledge database storing a second expression of a medical condition corresponding to the medical information, wherein the second expression is in a second expression category; and generating a medical condition inquiry report having the medical information with the second expression.

In some embodiments, the method further comprises: providing an inquiry framework for storing a dialog theme having a plurality of inquiry subjects; and managing the dialog with the patient based on the inquiry subjects of dialog theme.

Optionally, managing the dialog further comprises generating a first inquiry question, with expressions in the first expression category, relating to a first inquiry subject.

Optionally, managing the dialog further comprises detecting responsiveness of the first inquiry subject by the response from the patient.

Optionally, managing the dialog further comprises, upon detection of responsiveness to the first inquiry subject, generating a second inquiry question, with expressions in the first expression category, relating to a second inquiry subject.

Optionally, managing the dialog further comprises, upon detection of responsiveness to all inquiry subjects of the dialog theme, ending the dialog with the patient.

Optionally, the first expression category includes expressions in plain languages and the second expression category includes expressions in academic language.

BRIEF DESCRIPTION OF DRAWINGS

A more particular description of the embodiments will be rendered by reference to specific embodiments illustrated in the appended drawings. Given that these drawings depict only some embodiments and are not therefore considered to be limiting in scope, the embodiments will be described and explained with additional specificity and details through the use of the accompanying drawings, in which.

DETAILED DESCRIPTION

The disclosure will be described hereinafter with reference to the accompanying drawings which illustrate embodiments of the disclosure. This disclosure can, however, be implemented in many other forms and shall not be construed as limited to the illustrated embodiments set forth herein. In the specification, similar numerals represent similar components.

The terms used herein are merely for describing specific embodiments, and are not intended to limit the disclosure.

As used herein, the singular forms "a" and "an" are intended to include the plural forms as well, unless otherwise indicated clearly in the context. It is to be further understood that the terms "comprise" and/or "include" used herein indicate the presence of the described features, entirety, steps, operations, elements and/or components, but do not exclude the presence or addition of one or more other features, entirety, steps, operations, elements, components and/or combinations thereof.

Unless otherwise defined, all the terms (including technical and scientific terms) used herein have the same meaning as commonly understood by one of ordinary skill in the art. It is to be further understood that the terms should be interpreted as having a meaning that is consistent with their meaning in the context of the specification and in the relevant art rather than in an idealized or overly formal sense unless expressly so defined here.

In the disclosure, "preset", "predetermine" and the like may be a condition that a value and a parameter is pre-stored in the machine-aided dialog system, or a condition that a group of or multiple groups of values and parameters is pre-stored in the machine-aided dialog system and then is selected for use, or a condition that a value and a parameter is selectively input to the machine-aided dialog system when in use, or a condition that a value and a parameter stored in the machine-aided dialog system is updated in real time or regularly.

In the disclosure, "term" and "expression" may refer to a unit of language for representing a certain meaning, which may be in the form of either: one word, or several words that are put together or in a particular pattern.

The disclosure will be described hereinafter in combination with the accompanying drawings and with reference to the embodiments of the disclosure.

It is to be noted that the disclosure is described in a context of existence of medical condition preliminary inquiry carried out by a doctor when treating a patient. However, it is conceivable that the embodiments of the disclosure are not limited to be applied to the medical condition preliminary inquiry, but to any application scenario where information is collected via the man-machine dialog.

Figure 1:
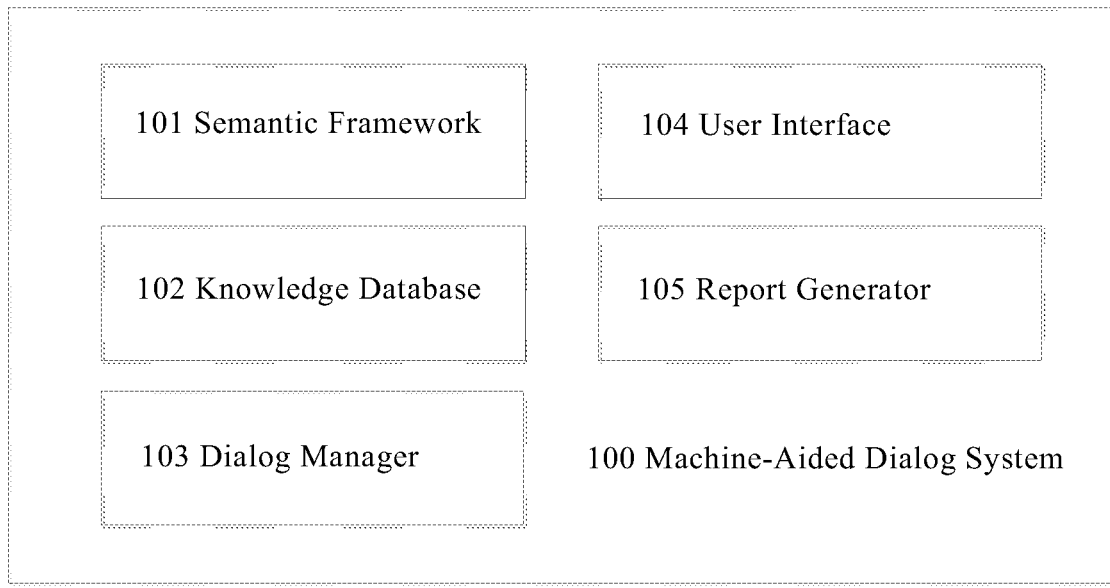
FIG. 1 illustrates a schematic diagram of a machine-aided dialog system according to an embodiment of the disclosure.

FIG. 1 illustrates a schematic diagram of a machine-aided dialog system according to at least one embodiment of the disclosure. The illustrated machine-aided dialog system 100 includes a semantic framework 101, a knowledge database 102 and a dialog manager 103.

The semantic framework 101 is configured to provide one or more dialog themes.

For example, in the medical field, a dialog theme may be a theme relating to a medical condition inquiry and the contents concerned by a doctor in the inquiry, i.e. inquiry subjects, include a patient's name, gender, age, chief complaint, history of present illness, history of previous illness, and allergic history, etc. For a medical condition inquiry, an inquiry framework, similar to the semantic framework 101, may be configured to store one or more dialog themes, each having a plurality of inquiry subjects.

The knowledge database 102 is configured to store semantic knowledge, and the semantic knowledge includes at least one group of content-related characters, words, phrases, sentences, paragraphs or a combination thereof.

The dialog manager 103 is configured to manage a dialog according to one or more dialog themes determined by the semantic framework 101. Upon the determination that a dialog theme have been completed according to a preset condition for dialog ending, the dialog theme is ended, or otherwise, the dialog needs to be managed continuously till all the work for collecting inquiries and responses is finished.

For example, in the medical field, a dialog may include inquiring the name, gender, age, chief complaint, history of present illness, history of previous illness, allergic history and the like of a patient, and collecting responses from the patient based on all the inquiry questions.

For example, the semantic knowledge stored in the knowledge database 102 is medical information, and the knowledge database may be referred to as a medical knowledge database. The medical information may include, for example, at least one of the followings: description of various disease symptoms, the name of a disease, the cause of the disease, a treatment method of the disease, and a drug for treating the disease. The medical information in the knowledge database may be expressed in academic or professional language which is used in medical reports.

The dialog manager 103 may inquire according to one or more predetermined dialog themes. The dialog manager 103 may acquire one or more question expressions of one or more predetermined dialog themes from the knowledge database 102 to make an inquiry.

In some embodiments, the dialog manager 103 may generate one or more question expressions based on a received response expression. The dialog manager 103 may find an inquiry question that requires user's clarification based on the received response expression and the semantic knowledge stored in the knowledge database 102.

For example, medical information at least includes a name of a disease and a description of a disease symptom. When the chief complaint of a patient is "cough", the dialog manager 103 may continue to ask "when does the cough start?", "have you ever contacted a cough patient?", "is the cough paroxysmal or continuous", "is there any expectoration", "does it attack mainly in the daytime or in the nighttime", "is there any pain in a throat", and the like, thereby generating one or more question expressions for a relevant dialog theme. In one example, according to a received response expression "having a little cough recently" and according to a semantic context and/or syntactic structure in the semantic knowledge, the dialog manager 103 extracts a keyword "cough" from the response expression; and meanwhile, one or more question expressions are generated according to the keyword "cough" in the response expression and a preset expression generation template. In this way, the dialog manager 103 extracts medical information of the patient based on the response from the patient. Optionally, a semantic analyzer, or natural language processor 10314, may be provided to extract such medical information of the patient based on the response from the patient.

According to one embodiment of the disclosure, the dialog efficiency and accuracy of the machine-aided dialog system can be greatly improved by virtue of the semantic knowledge in the knowledge database, and thus a dialog record with a high reference value is generated.

Optionally, the condition for dialog ending may be that: a response expression received by the dialog manager 103 contains a preset ending keyword, or contains a character, a word, a phrase, a sentence or a combination thereof that meets a preset matching relationship with the ending keyword.

For example, when "the symptom of the disease has been completely described" appears in the response expression, the dialog may be ended.

Optionally, the condition for dialog ending may be that: the number of times that the dialog manager 103 generates a question expression under a dialog theme reaches to a preset value, and a response expression corresponding to the newly generated expression is received within a preset time.

For example, under a dialog theme, the question depth preset by the dialog manager 103 is 10 (i.e., making 10 rounds of dialog), and all the questions in the 10 rounds of dialog are replied by response expressions.

Optionally, the condition for dialog ending may be that: the number of times that the dialog manager 103 generates a question expression under a dialog theme reaches to a preset value, and no response expression is received for a preset time after a latest question expression is generated and is sent.

For example, under a dialog theme, the condition for dialog ending may be set as follows: the question depth preset by the dialog manager 103 is 10 (i.e., making 10 rounds of dialog), and no response expression replying to the question expression in the tenth round is received within a preset time such as 2 min after a latest question expression (i.e., the question expression in the tenth round) is generated and is sent.

Optionally, the condition for dialog ending may also be that: one or more dialog themes provided by the semantic framework are all completed.

For example, three dialog themes are provided by the semantic framework, and each round of question expression in each dialog theme has got a response.

Optionally, the condition for dialog ending may also be that: no question expression is received for a preset time.

For example, under a dialog theme, the question depth preset by the dialog manager 103 is 10 (i.e., making 10 rounds of dialog), and after a question expression in the fifth round is generated and is sent, a response expression replying to a question expression in the fifth round is not received within a preset time such as 3 min. Such a case appears possibly because the accuracy and content of a question expression after multiple rounds of dialog go beyond the knowledge category of the user, or the preset question depth is too high so that a response expression has been given clearly and completely under the dialog theme without needing so many rounds of dialog.

Optionally, the condition for dialog ending may also be that: no response expression related to a keyword of a question expression is received for consecutive preset number of times.

For example, for the keyword "cough" in multiple question expressions, the contents in multiple response expressions relate to travel, driving, swimming or the like, which are irrelevant to the cough.

For example, in a medical condition preliminary inquiry, the dialog manager may be configured to detect responsiveness of the inquiry subjects of a dialog theme based on the response from the patient. Upon detection of responsiveness to an inquiry subject, e.g. whether an inquiry subject is completed by the response of the patient, the dialog manager generates questions relating to the next inquiry subject until all the inquiry subjects in the dialog theme are completely. The dialog manager may then determine that the dialog is ended.

In some embodiments, the machine-aided dialog system 100 further includes a man-machine interface 104, i.e. a user interactive interface. The man-machine interface 104 is configured to present, in response to the control of the dialog manager, one or more question expressions based on the dialog theme and collect a response expression.

For example, a question expression may be presented as voice, or displayed in an interface, or presented as voice combined with an interface, etc.

For example, a response expression may be collected by identifying a voice input of a user or an input of the user on a display interface or the combination of the both.

For example, the input on the display interface may be a selection for an option, such as inputting the gender by selecting "male" or "female", and may also be a character input, for example, by replying "male" or "female" via voice, all of which are not limited herein.

In some embodiments, the machine-aided dialog system 100 further includes a report generator 105, configured to generate a report based on the dialog contents and the response expressions. The report may include the one or more dialog themes determined by the semantic framework 101.

Taking a medical dialog theme as an example, the report may include inquiry subjects, for example, the name, gender, age, chief complaint, history of present illness, history of previous illness, allergic history and the like of a patient, as well as an input provided by the user for these questions. The generated report may be printed and/or sent to a medical information system of a doctor.

For example, in a medical dialog theme, a generated report is as follows:
Gender: female;
Age: 18; and
Chief complaint: cough is paroxysmal and continuous for a day and mainly takes place in the nighttime without any expectoration.

By generating and/or printing the report, the doctor may be assisted to make a diagnosis and thus the efficiency of the diagnosis is improved.

Figure 2:
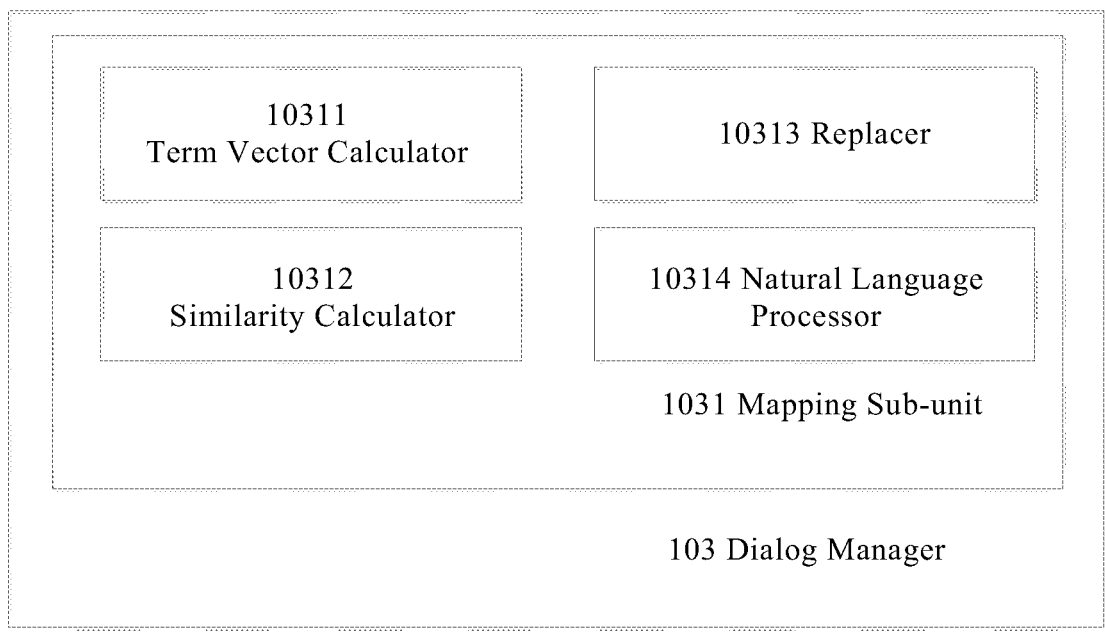
FIG. 2 illustrates a block diagram of a dialog manager of a machine-aided dialog system according to an embodiment of the disclosure.

FIG. 2 illustrates a block diagram of a dialog manager of a machine-aided dialog system according to an embodiment of the disclosure.

As shown in FIG. 2, the dialog manager 103 further includes a mapping sub-unit 1031, configured to map a term in a response expression into a corresponding expression of the semantic knowledge.

It is easily understood that, in a machine-aided dialog, a response given by a user such as a patient may be in oral language rather than in a professional or academic language, which may affect the readability or professionality of a dialog record or report. The problem can be solved or improved by mapping the oral expression into a corresponding professional expression of the semantic knowledge.

Specifically, the mapping sub-unit 1031 further includes: a term vector calculator 10311, a similarity calculator 10312 and a replacer 10313. The term vector calculator 10311 is configured to calculate a term vector of each term in a term set, where the term set includes a set of predetermined expressions of the sematic knowledge, and a set of terms in a response of a user serviced by the machine-aided dialog system. The similarity calculator 10312 is configured to respectively calculate similarities between a term in the response expression and each of expressions in the set of predetermined expressions according to the term vector of the term and term vectors of all expressions in the set of predetermined expressions. The replacer 10313 is configured to replace, in response to that the calculated similarity meets a threshold condition, the term in the response expression into a corresponding expression of the semantic knowledge.

In some embodiments, the mapping sub-unit 1031 further includes a natural language processor 10314, configured to identify a term in the response expression based on natural language processing. For example, English word or text segmentation may be performed based on stemming or lemmatization. For example, Chinese word segmentation and the like may be performed via a mechanical word segmentation algorithm (which is a word segmentation method based on character string matching), a statistic word segmentation algorithm based on a n-gram grammar, a word segmentation algorithm based on a hidden Markov model, a word segmentation algorithm based on a conditional random field, and the like, so that a sequence composed of a plurality of vocabularies is split into individual terms.

For example, a sentence "I suffer from diarrhea seriously" is segmented into three terms, i.e., "I", "suffer from diarrhea" and "seriously". Of course, besides this example, a sentence in a response expression may be segmented in other appropriate manners in the art and identified into terms. For example, the sentence is identified based on context and database matching, which is not limited herein.

In one example, all identified terms may be filtered to screen oral expressions out. For example, as to the "suffer from diarrhea" in the above sentence, mapping is performed on a term vector of this term only.

In one example, no filtering is made and all identified terms are subjected to the mapping processing. Some terms such as "I" have no terminology with a high similarity, and thus the result of mapping these terms may be that the terms are not replaced.

For a calculation manner of a term vector, in one embodiment of the disclosure, it is assumed that each term in a term set indicates a multi-dimensional Gaussian distribution and the mean value of the multi-dimensional Gaussian distribution is taken as the term vector of this term.

For example, it is assumed that each term w in a term set represents a multi-dimensional Gaussian distribution $f(w) \sim N(\mu_w, \Sigma_w)$, where the $\mu_w$ and the $\Sigma_w$ respectively represent the mean value and the covariance of the multi-dimensional Gaussian distribution of the term w. In order to simplify the model and the calculation, the $\Sigma_w$ is a diagonal matrix. The mean value and the variance of a multi-dimensional Gaussian distribution corresponding to each term need to be calculated, and in the disclosure Stochastic Gradient Descent (SGD) is applied to a target function. Here, a loss function is defined as the target function. The loss function $L(.,.,.)$ is expressed as follows:

$$L(w, c_p, c_n) = \max(0, 1 - S(w, c_p) + S(w, c_n)) \quad (1)$$

The term cp and the term cn both are elements in a term set. The term cp is a term in context of the term w in all response expressions of all users of the machine-aided dialog system 100, the term cn is a term not appearing in the context of the term w in any response expression of all users of the machine-aided dialog system, and the function $S(.,.)$ represents a similarity calculation function. Provided that the terms w1 and w2 are given, a similarity between the w1 and the w2 is calculated as follows:

$$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx \quad (2)$$

$$= \frac{1}{2} \{ tr(\Sigma_{w_1}^{-1} \Sigma_{w_2}) + (u_{w_1} - u_{w_2})^T \Sigma_{w_1}^{-1} (u_{w_1} - u_{w_2}) -$$

$$\log \frac{\det(\Sigma_{w_2})}{\det(\Sigma_{w_1})} - d \}$$

The tr( ) represents calculation of a trace of the matrix, the $\Sigma^{-1}$ represents an inversion of the matrix, the det represents calculation of a value of a determinant, and the d represents a constant irrelevant to the µ and the $\Sigma$.

By designing an optimal loss function $L(.,.,.)$, a similarity between a term in the context of the w and the w is at least higher than a similarity between a term not in the context of the w and the w.

The mean value $\mu_w$ of the Gaussian distribution of the term w, the mean value $\mu_{cp}$ of the Gaussian distribution of the term cp and the mean value $\mu_{cn}$ of the Gaussian distribution of the term cn are calculated (such as by using the SGD method) by substituting the formula (2) to the formula (1) when L is minimum, and the mean values are respectively taken as term vectors of the terms w, cp and cn. The above operations are repeated till the term vectors of all terms in the term set are obtained.

In this embodiment of the disclosure, data samples on which the calculation of the term vectors is relied are all response expressions received by the machine-aided dialog system 100. It is easily understood that a certain accumulated amount of the response expressions is needed to take as the data samples, and the larger the better. At an initial stage, some response expressions obtained by a system test may be pre-stored by the system 100 to take as the samples, or response expressions selected by a technical expert in related art may be taken as the samples. Along with the use of the system, the samples are expanded. The predetermined expressions are also included in the samples.

For the calculation manner of a term vector, in another embodiment of the disclosure, a term-term matrix is decomposed, a term is at least partially mapped to a potential semantic space based on an Explicit Semantic Analysis (ESA) to obtain a vector of this term in the potential semantic space and thus the vector is taken as a term vector of this term. The Explicit Semantic Analysis (abbreviated as ESA) is to respectively map terms to a high dimensional semantic concept space, where the meaning of each term represents a high dimensional vector and each dimension is a concept in the semantic concept space. The ESA method calculates the similarity by comparing with weight vectors of a wiki document related to the terms.

For example, Wikipedia is taken as high dimensional semantic concept space, each concept in Wikipedia is represented by a term vector in this disclosure, a vector of the term vector is a weight value obtained via a term frequency-inverse document frequency (tf–idf) model, and the weight values indicate the association between terms and concepts.

It is easily understood that the high dimensional semantic concept space is not limited to Wikipedia, and a knowledge base such as Baidupedia, hudong and Wolfram|Alpha is also applicable.

In one embodiment of the disclosure, the ESA is applied to term mapping, and the specific process is as follows:

It is assumed that the term-term matrix is represented by a matrix M, and the matrix M may be decomposed into a product of two k-order matrixes as follows:

$$M \approx P^T W \quad (3)$$

$M \in R m \times m$, $M_{i,j}$ is a tf–idf weight of the term vj in the term vi, and the ith column in the matrix P is a vector of the ith term in the potential semantic space. $P \in R k \times m$, $W \in R k \times m$, and the following target function is designed to calculate P and W.

$$L = \min_{P,W} \sum_{i=1}^{n} \sum_{j=1}^{m} (M_{i,j} - P_i^T W_j)^2 + \alpha \sum_{i=1}^{n} \sum_{f=1}^{n} E_{i,f} \|P_i - P_f\|_F^2 + \lambda (\|P\|_F^2 + \|W\|_F^2) \quad (4)$$

Here, V={v1, v2, vm} represents the term set, vi and vj (1≤i, j≤m) each represents a single term, Ei,j is a similarity between the terms vi and vj (such as a similarity based on the Wikipedia, etc.), ‖•‖2F is a Frobenius norm, α and λ are preset non-negative parameters, α is for controlling the importance of an ESA result, λ is for controlling the magnitude of P and W. ‖P‖F2+‖W‖F2 is for preventing overfitting, P∈Rk×m, W∈Rk×m, and R is a real number. According to the formula (3) and the formula (4), P is calculated (by using the SGD) under a condition in which the formula (2) is minimum, and thus a term vector $P_i$ of the term vi and a term vector $P_j$ of the term vj are obtained.

When P is calculated specifically, partial derivatives of P and W need to be obtained by using the formula (2) first.

$$\frac{\partial L}{\partial P_i} = -2 \sum_{j=1}^{n} (M_{i,j} - P_i^T W_j) W_j + 2\alpha \sum_{f=1}^{n} (E_{i,f})(P_i - P_f) + 2\lambda P_i \quad (5)$$

$$\frac{\partial L}{\partial W_i} = -2 \sum_{i=1}^{n} (M_{i,j} - P_i^T W_j) P_i + 2\lambda W_j \quad (6)$$

Based on the formulas (5) and (6), P may be obtained by SGD, i.e., a vector expression of each term in the potential semantic space.

The vector of each term is obtained via the above method, in which the term vector of the term vi is $P_i$, and the term vector of the term vj is $P_j$. In a case that the similarity (the δ is a preset threshold) between the term vectors of the term vi and the term vj is $P_i^T P_j \geq \delta$, the vi and the vj express the same meaning. In this way, the oral term vi in the response expression may be replaced with the expression vj.

This embodiment of the disclosure describes how to solve by using the SGD method which is merely adopted herein as an example. An iterative solving method is also applied to the disclosure, such as Batch Gradient Descent (BGD), Mini-Batch Gradient Descent (MBGD), conjugate gradient, and quasi-Newton.

When the similarity is calculated, various similarity calculation methods may be adopted, such as Cosine, Cityblock, Euclidean, Mahalanobis, Minkowski and Chebychev.

In one embodiment of the disclosure, a cosine similarity is adopted to represent the similarity between the term vectors of the terms vi and vj.

In this embodiment of the disclosure, the term vector calculator, the similarity calculator, the replacer and the natural language processor may be implemented by a processor configured to execute an instruction of a program, or these entities may be implemented in a programmable manner by one or more hardware modules or integrated circuits.

The above mapping method can contribute to the improvement of the readability and the professionality of a dialog record.

As described above, in this embodiment of the disclosure, the conversion between the oral language/plain language and the term in the machine-aided dialog is illustrated via the mapping sub-unit used in the machine-aided dialog system. It is easily understood that the mapping sub-unit is not limited to the above-described specific application, but may also be widely applied to various man-machine dialog applications (such as language translation, medical diagnosis and virtual assistant).

Correspondingly, an embodiment of the disclosure further provides a mapping apparatus. The mapping apparatus is configured to convert an oral language into a term (that is, a written language including a knowledge base for semantic knowledge corresponding to terms in a man-machine dialog scenario, where the knowledge base may include at least one group of characters, words, phrases, sentences, paragraphs or a combination thereof relevant to the content of the man-machine dialog scenario) in a man-machine dialog, so as to accurately and clearly understand an intention of a user.

A logic structural design of the mapping apparatus may be referred to the above-mentioned description of the mapping sub-unit 1031.

Figure 5:
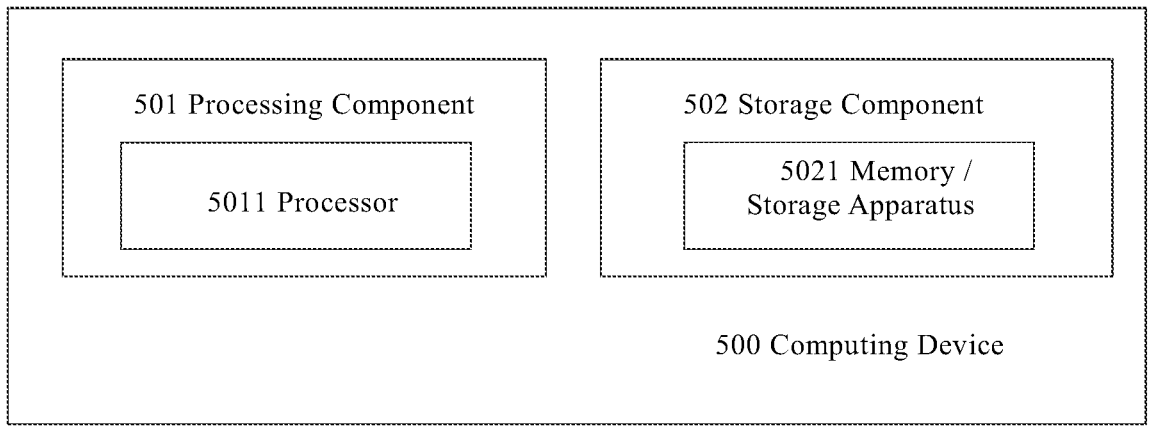
FIG. 5 illustrates a schematic diagram of a machine-aided dialog apparatus according to an embodiment of the disclosure.

A structural design of each of physical entities of the mapping apparatus may be referred to FIG. 5.

The mapping apparatus and the sub-unit (the semantic framework, the knowledge database, the dialog manager and the mapping sub-unit) may be implemented by using a processor configured to execute an instruction of a program, or these entities may be implemented in a programmable manner by one or more hardware modules or integrated circuits.

Correspondingly, an embodiment of the disclosure provides a mapping method. The mapping method is for converting an oral language into a term (that is, a written language including a knowledge base for semantic knowledge corresponding to terms in a man-machine dialog scenario, where the knowledge base may include at least one group of characters, words, phrases, sentences, paragraphs or a combination thereof relevant to the content of the man-machine dialog scenario) in a man-machine dialog, so as to accurately and clearly understand an intention of a user.

The process of the mapping method may be referred to the above-mentioned working process of the mapping sub-unit 1031.

Figure 3:
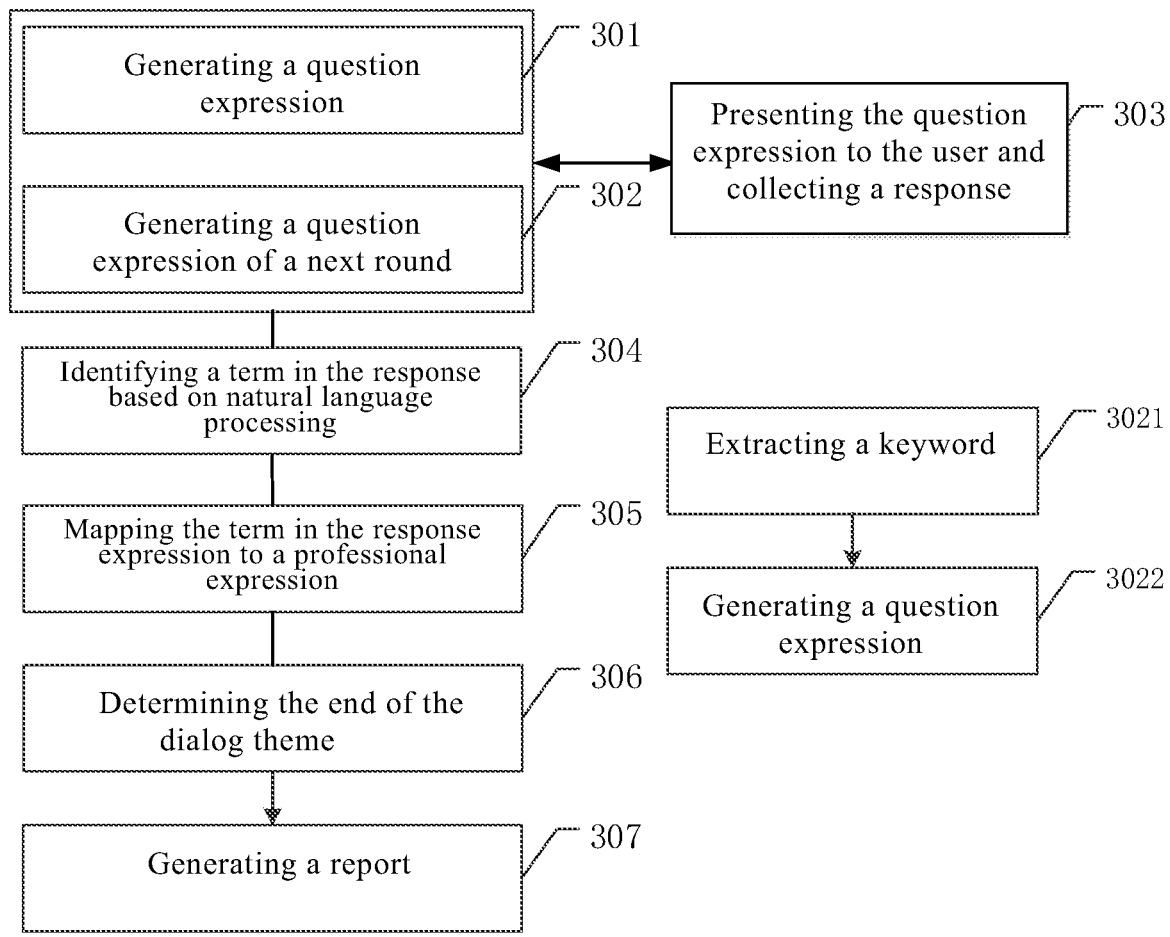
FIG. 3 illustrates a schematic flowchart of a dialog managed according to a dialog theme provided by a semantic framework according to an embodiment of the disclosure.

FIG. 3 illustrates a schematic flowchart of a dialog 300 managed according to a dialog theme provided by a semantic framework according to an embodiment of the disclosure. The machine-aided dialog apparatus described in FIG. 1 may be used in the machine-aided dialog method. The method may include the following steps: at Step 300, a dialog is managed according to a dialog theme provided by a semantic framework. In the step 301, one or more question expressions for any theme in one or more dialog themes are generated based on semantic knowledge obtained from a knowledge database. At Step 302, a question expression for a next round of dialog is generated according to the semantic knowledge obtained from the knowledge database and a received response expression.

In some embodiments, in a sub-step 3021 of the step 302, a keyword in the response expression is extracted according to the received response expression and according to a semantic context and/or syntactic structure in the semantic knowledge.

In some embodiments, in a sub-step 3022 of the step 302, one or more question expressions are generated according to the keyword in the response expression and a preset expression generation template.

In some embodiments, a dialog may be refined according to the semantic knowledge in the knowledge database 102.

For example, the semantic knowledge is medical information. When a chief complaint input by a user is "cough", an inquiry question that requires user's clarification may be found from the semantic knowledge stored in the knowledge database 102. For example, the semantic knowledge relevant to the cough is that the clinical symptoms of the cough include whether the cough is paroxysmal or continuous, whether there is any expectoration, whether it mainly attacks in the daytime or in the nighttime, whether there is any pain in a throat, and the like, based on which relevant question expressions may be generated.

By virtue of the semantic knowledge in the knowledge database 102, the dialog fineness of the machine-aided dialog method may be obviously improved. Meanwhile, the difficulty of a user to make a dialog may be reduced, and thus a dialog record with a high reference value is generated.

At Step 303, a question based on the dialog content is presented to the user and a response expression is collected. The presentation may appear as voice, or an interface, or voice combined with an interface, etc. The collection may be carried out by identifying a voice input of the user or the input on a display interface or the input combined both. The input on the display interface may be a selection for an option, such as inputting the gender by selecting "male" or "female", and may also be a character input, for example, by replying "male" or "female" via voice, all of which are not limited here.

In some embodiments, at Step 304, a term in a response expression is identified based on natural language processing. For example, a sentence "I suffer from diarrhea seriously" is segmented into three terms, i.e., "I", "suffer from diarrhea" and "seriously'. Of course, besides this example, the sentence in the response expression may be segmented by other appropriate manners in the art and identified into terms. For example, the sentence is identified based on context and database matching, which is not limited here. In one example, all identified terms may be filtered to select oral expressions. For example, as to the term "suffer from diarrhea" in the above sentence, mapping is performed on a term vector of this term only. In one example, no filtering is made and all identified terms are subjected to the mapping. Some terms such as "I" have no terminology with a high similarity, and thus the result of mapping these terms may be that the terms are not replaced.

In some embodiments, at Step 305, the term in the response expression is mapped into a professional expression. A non-professional expression such as words or expressions in oral language or plain language in the response expression of the user is converted into an expression in professional language or academic language, thereby improving the readability or the professionality of a dialog report or a report. For example, a patient may reply that "I have the runs seriously" in a response to an inquiry question, instead of "I suffer from diarrhea seriously" using medical term "diarrhea". In some examples, the medical condition inquiry apparatus may comprise a semantic analyzer that extracts "have the runs" from the user response and a report generator that generates "diarrhea" in the medical condition inquiry report.

At Step 306, the dialog theme is ended once a dialog theme is determined to be completed in response to that a preset condition for dialog ending is met.

For example, the condition for dialog ending may be that: the response expression received by the dialog manager 103 contains a preset ending keyword, or contains a character, a word, a phrase, a sentence or a combination thereof that meets a preset matching relationship with the ending keyword.

For example, the condition for dialog ending may be that: the number of times that the dialog manager 103 generates a question expression under a dialog theme reaches to a preset value, and a response expression corresponding to the newly generated expression is received within a preset time.

For example, the condition for dialog ending also may be that: the number of times that the dialog manager 103 generates a question expression under a dialog theme reaches to a preset value, but no response expression is received for a preset time after a latest question expression is generated and is sent.

For example, the condition for dialog ending may also be that: one or more dialog themes provided by the semantic framework are completed.

For example, the condition for dialog ending may also be that: no response expression is received for a preset time.

For example, the condition for dialog ending may also be that: no response expression associated with the keyword of a question expression is received for consecutive preset number of times.

In some embodiments, at Step 307, the report is generated based on the dialog content and the response expression. The report may include the determined one or more dialog themes.

For example, in an inquiry, the report may include, for example, a patient's name, gender, age, chief complaint, history of present illness, history of previous illness, allergic history and the like, as well as a response provided by the user for these questions. The generated report may be printed and/or sent to a medical information system of a doctor.

For example, in a medical dialog theme, a generated report is as follows:
Gender: female;
Age: 18; and
Chief complaint: cough is paroxysmal and continuous for a day and mainly takes place in the nighttime without any expectoration.

In some embodiments, a medical condition inquiry apparatus maybe provided employing an embodiment of the machine-aided dialog system. The medical condition apparatus may comprise a user interactive interface 104 for providing a dialog with a patient, including inquiring a patient's health status and receiving a response from the patient; a semantic analyzer 10314, for extracting medical information of the patient based on the response from the patient, wherein the response from the patient is a first expression in a first expression category; a medical knowledge database 102 storing a second expression of a medical condition corresponding to the medical information, wherein the second expression is in a second expression category; and a report generator 105, for generating a medical condition inquiry report having the medical information with the second expression.

In some embodiments, the medical condition inquiry apparatus may further comprise an inquiry framework for storing a dialog theme having a plurality of inquiry subjects; and a dialog manager for managing the dialog with the patient based on the inquiry subjects of the dialog theme. The dialog manager may be configured to generate inquiry questions, with expressions in the first expression category, relating to inquiry subjects. The dialog manager may end the dialog with the patient when all inquiry subjects of the dialog theme are completed. The first expression category may include expressions in plain languages and the second expression category includes expressions in academic language.

By generating and/or printing an inquiry report, the doctor may be assisted to make a diagnosis and thus the efficiency of the diagnosis is improved.

Figure 4:
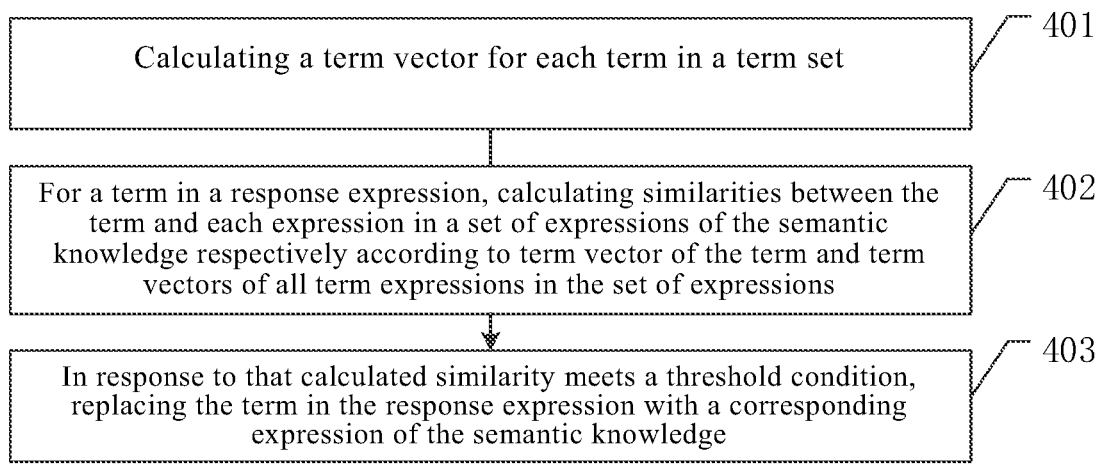
FIG. 4 illustrates a schematic flowchart of a mapping method according to an embodiment of the disclosure.

FIG. 4 illustrates a schematic flowchart of a mapping method according to an embodiment of the disclosure. At Step 401, a term vector of each term in a term set is calculated, where the term set includes a set of predetermined expressions, and a set of terms in a response of a user serviced by the machine-aided dialog system. At Step 402, for the terms in the response expression, similarities between the terms and each expression in set of predetermined expressions of the semantic knowledge are respectively calculated according to term vectors of the term and term vectors of all term expressions in the set of expressions. At Step 403, in response to that the calculated similarity meets a threshold condition, a term in a response expression is replaced with a corresponding expression of the semantic knowledge.

In one embodiment, the similarity adopted in the disclosure is a cosine similarity between the term vectors. Other similarity calculation methods may also be applied to this embodiment of the disclosure, such as Cityblock, Euclidean, Mahalanobis, Minkowski and Chebychev.

The term vector of the term vi is $P_i$, and the term vector of the term vj is $P_j$. In a case that the similarity between the term vectors of the term vi and the term vj is $P_i^T P_j \geq \delta$ ($\delta$ is a preset threshold), it is considered that the vi and the vj express the same meaning. In this way, the oral expression vi in the response expression may be replaced with the professional expression vj. The detailed description of the calculation manner of the term vector is provided above in combination with FIG. 2 and will not be repeated here.

In this way, the readability and professionality of the dialog record are improved.

It is to be understood and noticed that each aspect of the theme described herein is not limited by the illustrated actions and/or is not limited by a sequence of the actions. In some embodiments, these actions are carried out according to a sequence. However, in other embodiments, these actions may be carried out concurrently or according to another sequence and/or may be carried out together with other actions not shown and described here. In addition, not all of the illustrated actions are necessary to implement the method according to each aspect of the theme described here. Besides, it is to be understood and noticed by a person skilled in the art that the method can be shown as a series of relevant states by a state chart or can be shown as an event.

FIG. 5 illustrates a schematic diagram of a machine-aided dialog apparatus according to another embodiment of the disclosure, which includes an exemplary computing device 500 representative of one or more systems and/or devices capable of implementing various technologies described herein. The computing device 500 may be, for example, a terminal device, an on-chip system and/or any other suitable computing devices or computing systems.

The exemplary computing device 500 shown in the figure includes a processing component 501 and a storage component 502 that are communicated and coupled to one another.

Further, the computing device 500 may further include an Input/Output (I/O) interface.

Although not shown, the computing device 500 may include a system bus or other data and command transmission systems so as to couple various components to each other. The system bus may include any one bus structure or any combination of different bus structures. The bus structure may be, for example, a memory bus or a memory controller, a peripheral bus, a universal serial bus, and/or any one processor or local bus using various bus architectures. Other examples are further conceivable such as control and data bus.

The processing component 501 represents a function of executing one or more operations by using hardware. Therefore, the processing component 501 includes one or more processors 5011. The processor 5011 may be a logic operation component having a data processing capability and/or a program execution capability, such as a Central Processing Unit (CPU) or a Field Programmable Gate Array (FPGA) or a Microprogrammed Control Unit (MCU) or a Digital Signal Processor (DSP) or an Application Specific Integrated Circuit (ASIC).

In this embodiment of the disclosure, the processor 5011 is not limited by the material forming the processor or by a processing mechanism adopted therein. For example, the processor may be composed of (a plurality of) a semiconductor and/or transistor (such as an electronic Integrated Circuit (IC)).

In this embodiment of the disclosure, the storage component 502 shown in figure includes one or more memories/storage apparatuses 5021. The memory/storage apparatus 5021 represents a memory/storage capacity associated with one or more computer readable media. The memory/storage apparatus 5021 may include a volatile medium (such as a Random Access Memory (RAM)) and/or a non-volatile medium (such as a Read-Only Memory (ROM), a flash memory, an optical disc and a magnetic disk). The memory/storage apparatus 5021 may include a fixed medium (such as a RAM, a ROM, and a fixed hardware driver) and a removable medium (such as a flash memory, a removable hardware driver and an optical disc).

The storage component 502 is not limited to those described in the above embodiment. Other structures of the storage components 502 are also applicable to this embodiment of the disclosure, such as a virtual storage resource provided based on a cloud computing environment.

In this embodiment of the disclosure, the I/O interface represents a function that allows a user to input a command and information to the computing device 500 and further allows using various input/output devices to show the information to the user and/or other components or devices. An input device may be, for example, a keyboard, a cursor control device (such as a mouse), a microphone (such as for inputting a voice), a scanner, a touch function (such as being configured to detect the capacitance of a physical touch or other sensors), and a camera (which, for example, may detect a motion irrelevant to touch as a gesture by using a visible or invisible wavelength (such as an infrared frequency)), etc. An output device may be, for example, a display device (such as a display or a projector), a loudspeaker, a printer, a network card, a wireless network card, a Bluetooth module and a touch response device, etc.. Therefore, the computing device 500 may be configured in any of the manners described below so as to support the interaction of the user.

Various technologies can be described in a general context of software, hardware or program modules. Generally, these modules include a routine, a program, an object, an element, a component, a data structure and the like for executing a special task or implementing a special abstract data type. The terms "module", "function" and "component" used here generally represent software, fixture, hardware or a combination thereof. The technical features described here are independent of a platform, which means that these technologies may be implemented on various computing platforms having various processors.

The implementation of the described modules and technologies may be stored on a computer readable medium or transmitted across a computer readable medium. The computer readable medium may include various media that the computing device 500 can access. As an example rather than a limit, the computer readable medium may include a "computer readable storage medium" and a "computer readable signal medium".

Contrast to pure signal transmission, carrier or signal, the "computer readable storage medium" refers to a medium and/or a device capable of storing information permanently, and/or to a tangible storage apparatus. Therefore, the computer readable storage medium refers to a non-signal bearing medium. The computer readable storage medium may include, for example, a volatile medium, a non-volatile medium, a removable medium and an irremovable medium, and/or hardware such as a storage device which is implemented by a method or a technology adapted to store information (such as a computer readable instruction, a data structure, a program module, a logic element/circuit or other data). For example, the computer readable storage medium may include but is not limited to a RAM, a ROM, an EEPROM, a flash memory or other memory technologies, a CD-ROM, a digital universal disk (DVD) or other optical storage apparatuses, a hard disk, a cassette tape, a magnetic tape, a disk storage apparatus or other magnetic storage devices, or other storage devices, a tangible medium or a product adapted to store expected information and capable of being accessed by the computer.

The "computer readable signal medium" refers to a signal bearing medium for sending an instruction to hardware of the computing device 500 via a network. Typically, the signal medium may embody a computer readable instruction, a data structure, a program module or other data in a carrier, a data signal or a modulation data signal of other transmission mechanisms. The signal medium also includes any information transmission medium. The term "modulation data signal" refers to encode information in a signal in a manner to set or change one or more signals in the characteristics. As an example but not a limit, the communication medium includes a wired medium such as a wired network or a direct connection line or a wireless medium such as a sound, a Radio Frequency (RF), an infrared ray and other wireless media.

The foregoing combination may also be applicable for implementing the technologies and modules described in the disclosure. Hence, a software, hardware or program module and other program modules may be implemented as a computer readable storage medium and/or one or more instructions and/or logics carried out by one or more processors 5011. The computing device 500 may be configured to implement a specific instruction and/or function corresponding to the software and/or hardware module.

The technologies described herein may be supported by various configurations of the computing device 500, and are not limited to the specific examples described herein. The processing component 501 and the storage component 502 may further be implemented wholly or partially by using a distributed system on cloud.

Based on the above-mentioned computing device, an embodiment of the disclosure further provides a machine-aided dialog apparatus, which includes: an I/O interface, configured to receive an input and provide an output; a processor; and a memory, configured to store a computer executable instruction, the instruction being for, when being executed in the processor, implementing the method described according to FIG. 3 and/or FIG. 4.

An embodiment of the disclosure further provides a computer readable storage medium having stored a computer executable instruction, where the instruction being for, when being executed by a computing device, enabling the computing device to implement the method described according to FIG. 3 and/or FIG. 4.

Figure 6:
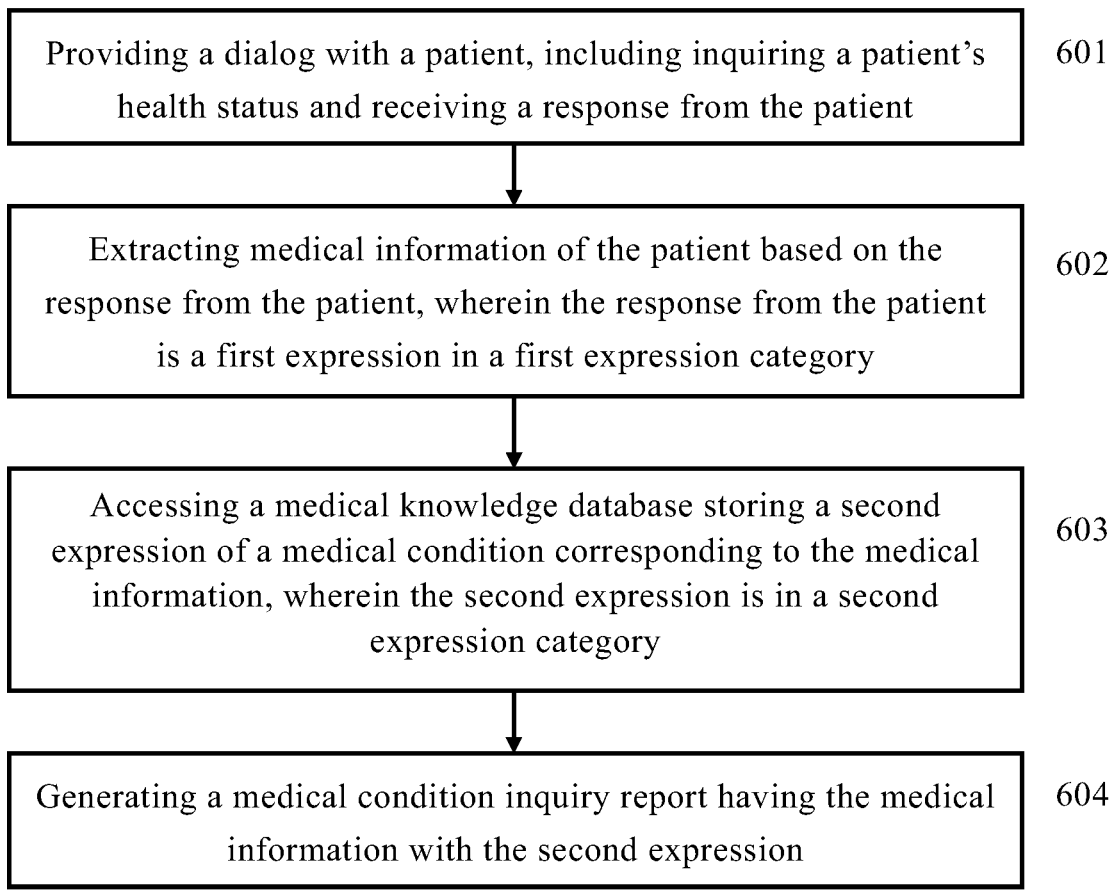
FIG. 6 illustrates a schematic flowchart of a method of medical condition inquiry according to an embodiment of the disclosure.

FIG. 6 illustrates a schematic flowchart of a method of medical condition inquiry according to an embodiment of the disclosure.

At step 601, it provides a dialog with a patient from a user interactive interface, including inquiring a patient's health status and receiving a response from the patient. The dialog may be provided by a machine-aided or computer-aided dialog system having an interactive interface. The interactive interface may include a microphone, a speaker and/or a camera for audio and/or video communication with the patient.

At step 602, it extracts medical information of the patient based on the response from the patient, wherein the response from the patient is a first expression in a first expression category. The response from the patient is processed by the system to extract the medical information. Other irrelevant information may be discarded. The response from the patient may be plain language, such as plain English language, describing his/her medical condition.

At step 603, the extracted medical information is further processed with a medical knowledge database. It accesses a medical knowledge database storing a second expression of a medical condition corresponding to the medical information, wherein the second expression is in a second expression category. The information stored in the medical knowledge database may include expressions of the medical condition described in academic language. The expressions in academic language may not be used commonly by the general public, but are efficient in communication among medical professionals, such as doctors and nurses.

At step 603, a medical condition inquiry report having the medical information with the second expression is generated. This report may be a formal inquiry report that could be reviewed by the doctor before seeing the patient, or while communicating with the patient.

In some embodiments, the method further comprises: providing an inquiry framework for storing a dialog theme having a plurality of inquiry subjects; and managing the dialog with the patient based on the inquiry subjects of dialog theme. Optionally, managing the dialog may further comprise generating a first inquiry question, with expressions in the first expression category, relating to a first inquiry subject; detecting responsiveness of the first inquiry subject by the response from the patient; upon detection of responsiveness to the first inquiry subject, generating a second inquiry question, with expressions in the first expression category, relating to a second inquiry subject; and upon detection of responsiveness to all inquiry subjects of the dialog theme, ending the dialog with the patient.

Various embodiments are described in the disclosure. It is to be understood that each embodiment described herein may be used independently or associatively with one or more other embodiments described herein.

According to the embodiments of the disclosure, a preliminary inquiry may help a doctor acquire the health status of a patient in advance, thereby optimizing the procedure of seeing the doctor, increasing the readability and professionality of a dialog record, and improving the diagnosis efficiency of the doctor.

Although the disclosure is described in combination with specific embodiments, it is to be understood by the person skilled in the art that many changes and modifications may be made and equivalent replacements may be made to the components without departing from a real scope of the disclosure. Besides, many modifications may be made without departing from a central scope so that the instruction is applicable to a special case. Therefore, the disclosure is not limited to the specific embodiments conceived as optimal modes for implementing the disclosure. On the contrary, the disclosure includes all embodiments falling into the scope of the appended claims.

The invention claimed is:

1. A machine-aided dialog system, comprising:
a semantic framework for providing a dialog theme;
a knowledge database for storing semantic knowledge, the semantic knowledge comprising at least one group of content-related expressions, wherein the semantic knowledge is obtained by a mapping apparatus implemented by a hardware circuit to map a term in a response expression into a corresponding express of the semantic knowledge; and
a dialog manager for managing a dialog according to the dialog theme provided by the semantic framework, wherein managing the dialog comprises: generating a question expression of the dialog theme based on the semantic knowledge acquired from the knowledge database, wherein the question expression is presented on a display interface; and ending the dialog theme upon determining that the dialog theme is completed in response to a dialog ending condition, wherein the dialog is to be output using the display interface;
wherein the mapping apparatus further comprises a term vector calculator for calculating a term vector of each term in a term set, wherein both a set of predetermined expressions of the semantic knowledge and a set of terms in the response expression are proper subsets of the term set, and the term vector calculator is further configured to decompose a term-term matrix, at least partially map a term to a potential semantic space based on an Explicit Semantic Analysis (ESA) to obtain a vector of the term in the potential semantic space and take the vector as a term vector of the term; and
wherein the term vector calculator calculates the term vector of each term in the term set in a following manner:

$$M \approx P^T W \quad (3)$$

$$\min_{P,W} \sum_{i=1}^{n}\sum_{j=1}^{m}(M_{i,j} - P_i^T W_j)^2 + \alpha \sum_{i=1}^{n}\sum_{f=1}^{n} E_{i,f}\|P_i - P_f\|_F^2 + \lambda(\|P\|_F^2 + \|W\|_F^2) \quad (4)$$

where V={v1, v2, ..., vm} represents the term set, $v_i$ and $v_j$ (1≤i, j≤m) each represents a single term, $M \in R^{m \times m}$ represents the term-term matrix, $M_{i,j}$ is a Term Frequency-Inverse Document Frequency (tf–idf) weight of the term $v_i$ in the term $v_j$, $E_{i,j}$ is a similarity between the terms $v_i$ and $v_j$, $\|\cdot\|_F^2$ is a Frobenius norm, α and λ are preset non-negative parameters, $P \in R^{k \times m}$, $W \in R^{k \times m}$, and R is a real number; and P is calculated under a condition in which the formula (4) is minimum according to the formula (3) and the formula (4), and a term vector $P_i$ of the term $v_i$ and a term vector $P_j$ of the term $v_j$ are obtained.

2. The machine-aided dialog system of claim 1, wherein managing the dialog further comprises: according to a received response expression, extracting a keyword from the received response expression based on a semantic context and/or syntactic structure in the semantic knowledge; and generating one or more question expressions according to the keyword in the response expression and a preset expression generation template.

3. The machine-aided dialog system of claim 1, wherein the mapping apparatus comprises:
a similarity calculator for respectively calculating similarities between a term in the response expression and each expression in the set of predetermined expressions according to a term vector of the term and term vectors of all expressions in the set of predetermined expressions; and
a replacer for replacing the term in the response expression with the corresponding expression of the semantic knowledge in response to the condition that the calculated similarity meets a threshold condition.

4. The machine-aided dialog system of claim 3, wherein the term vector calculator is further configured to indicate each term in the term set as a multi-dimensional Gaussian distribution and take a mean value of the multi-dimensional Gaussian distribution as a term vector of the each term.

5. The machine-aided dialog system of claim 4, wherein the term vector calculator calculates the term vector of each term in the term set in a following manner:
it is assumed that each term w in the term set represents a multi-dimensional Gaussian distribution $f(w) \sim N(\mu_w, \Sigma_w)$, where the $\mu_w$ and $\Sigma_w$ respectively represent a mean value and a covariance of the multi-dimensional Gaussian distribution of the term w, and $\Sigma_w$ is a diagonal matrix, $$L(w, c_p, c_n) = \max(0, 1 - S(w, c_p) + S(w, c_n)) \quad (1)$$

where $c_p$ and $c_n$ both are elements in the term set, $c_p$ is a term in context of the term w in all response expressions received by the machine-aided dialog system, $c_n$ is a term not appearing in the context of the term w in any response expressions received by the machine-aided dialog system, and function S(.,.) represents a similarity calculation function; and for given terms w1 and w2, a similarity between w1 and w2 is calculated as follows:

$$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx \quad (2)$$

$$= \frac{1}{2}\{tr(\Sigma_{w_1}^{-1}\Sigma_{w_2}) + (u_{w_1} - u_{w_2})^T \Sigma_{w_1}^{-1}(u_{w_1} - u_{w_2}) -$$

$$\log \frac{\det(\Sigma_{w_2})}{\det(\Sigma_{w_1})} - d\}$$

where tr( ) represents calculating a trace of the matrix, $\Sigma^{-1}$ represents an inversion of the matrix, det represents calculating a value of a determinant, and d represents a constant irrelevant to μ and Σ;
the mean value $\mu_w$ of the Gaussian distribution of the term w, the mean value $\mu_{c_p}$ of the Gaussian distribution of $c_p$, and the mean value $\mu_{c_n}$ of the Gaussian distribution of $c_n$ when L is minimum are calculated by substituting the formula (2) to the formula (1), and the mean values are respectively taken as term vectors of the term w, $c_p$ and $c_n$; and the above operations are repeated till the term vectors of all terms in the term set are obtained.

6. The machine-aided dialog system of claim 3, wherein the condition that the similarity meets the threshold condition comprises: a cosine similarity between the term vector of the term in the response expression and a term vector of the corresponding expression of the semantic knowledge is greater than or equal to a predetermined threshold.

7. A method of machine-aided dialog, comprising:
providing a semantic framework for providing a dialog theme;
providing a knowledge database for storing semantic knowledge, the semantic knowledge comprising at least one group of content-related expressions, wherein the semantic knowledge is obtained by a mapping apparatus implemented by a hardware circuit to map a term in a response expression into a corresponding express of the semantic knowledge; and
providing a dialog manager for managing a dialog according to the dialog theme provided by the semantic framework, wherein managing the dialog comprises: generating a question expression of the dialog theme based on the semantic knowledge acquired from the knowledge database, wherein the question expression is presented in a display interface; and ending the dialog theme upon determining that the dialog theme is completed in response to a dialog ending condition, wherein the dialog is to be output using the display interface;
wherein the mapping apparatus further comprises a term vector calculator for calculating a term vector of each term in a term set, wherein both a set of predetermined expressions of the semantic knowledge and a set of terms in the response expression are proper subsets of the term set, and the term vector calculator is further configured to decompose a term-term matrix, at least partially map a term to a potential semantic space based on an Explicit Semantic Analysis (ESA) to obtain a vector of the term in the potential semantic space and take the vector as a term vector of the term; and
wherein the term vector calculator calculates the term vector of each term in the term set in a following manner:

$$M \approx P^T W \quad (3)$$

$$\min_{P,W} \sum_{i=1}^{n} \sum_{j=1}^{m} (M_{i,j} - P_i^T W_j)^2 + \alpha \sum_{i=1}^{n} \sum_{f=1}^{n} E_{i,f} \|P_i - P_f\|_F^2 + \lambda (\|P\|_F^2 + \|W\|_F^2) \quad (4)$$

where $V=\{v1, v2, \ldots, vm\}$ represents the term set, $v_i$ and $v_j$ ($1 \le i, j \le m$) each represents a single term, $M \in R^{m \times m}$ represents the term-term matrix, $M_{i,j}$ is a Term Frequency-Inverse Document Frequency (tf–idf) weight of the term $v_j$ in the term $v_i$, $E_{i,j}$ is a similarity between the terms $v_i$ and $v_j$, $\|\cdot\|_F^2$ is a Frobenius norm, $\alpha$ and $\lambda$ are preset non-negative parameters, $P \in R^{k \times m}$, $W \in R^{k \times m}$, and R is a real number; and P is calculated under a condition in which the formula (4) is minimum according to the formula (3) and the formula (4), and a term vector $P_i$ of the term $v_i$ and a term vector $P_j$ of the term $v_j$ are obtained.

8. The method of claim 7, wherein managing the dialog further comprises: according to a received response expression, extracting a keyword from the received response expression based on a semantic context and/or syntactic structure in the semantic knowledge; and generating one or more question expressions according to the keyword in the response expression and a preset expression generation template.

9. The method of claim 7, wherein the mapping apparatus comprises:
a similarity calculator for respectively calculating similarities between a term in the response expression and each expression in the set of predetermined expressions according to a term vector of the term and term vectors of all expressions in the set of predetermined expressions; and
a replacer for replacing the term in the response expression with the corresponding expression of the semantic knowledge in response to the condition that the calculated similarity meets a threshold condition.

10. The method of claim 9, wherein the term vector calculator is further configured to indicate each term in the term set as a multi-dimensional Gaussian distribution and take a mean value of the multi-dimensional Gaussian distribution as a term vector of the each term.

11. The method of claim 10, wherein the term vector calculator calculates the term vector of each term in the term set in a following manner:
it is assumed that each term w in the term set represents a multi-dimensional Gaussian distribution $f(w) \sim N(\mu_w, \Sigma_w)$, where the $\mu_w$ and $\Sigma_w$ respectively represent a mean value and a covariance of the multi-dimensional Gaussian distribution of the term w, and $\Sigma_w$ is a diagonal matrix, $$L(w, c_p, c_n) = \max(0, 1 - S(w, c_p) + S(w, c_n)) \quad (1)$$

where $c_p$ and $c_n$ both are elements in the term set, $c_p$ is a term in context of the term w in all response expressions received by the machine-aided dialog system, $c_n$ is a term not appearing in the context of the term w in any response expressions received by the machine-aided dialog system, and function $S(.,.)$ represents a similarity calculation function; and for given terms w1 and w2, a similarity between w1 and w2 is calculated as follows:

$$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx \quad (2)$$

$$= \frac{1}{2} \left\{ tr(\Sigma_{w_1}^{-1} \Sigma_{w_2}) + (u_{w_1} - u_{w_2})^T \Sigma_{w_1}^{-1} (u_{w_1} - u_{w_2}) - \log \frac{\det(\Sigma_{w_2})}{\det(\Sigma_{w_1})} - d \right\}$$

where tr( ) represents calculating a trace of the matrix, $\Sigma^{-1}$ represents an inversion of the matrix, det represents calculating a value of a determinant, and d represents a constant irrelevant to $\mu$ and $\Sigma$;
the mean value $\mu_w$ of the Gaussian distribution of the term w, the mean value $\mu_{c_p}$ of the Gaussian distribution of $c_p$, and the mean value $\mu_{c_n}$ of the Gaussian distribution of $c_n$ when L is minimum are calculated by substituting the formula (2) to the formula (1), and the mean values are respectively taken as term vectors of the term w, $c_p$ and $c_n$; and the above operations are repeated till the term vectors of all terms in the term set are obtained.

12. The method of claim 9, wherein the condition that the similarity meets the threshold condition comprises: a cosine similarity between the term vector of the term in the response expression and a term vector of the corresponding expression of the semantic knowledge is greater than or equal to a predetermined threshold.

13. A machine-aided dialog device, comprising:
an I/O interface for receiving an input from a user and providing an output to the user;
a processor;
a memory for storing executable instructions, wherein the executable instructions upon execution by the processor causing the device to perform the method of claim 1.

14. A medical condition inquiry apparatus, comprising:
a user interactive interface, comprising a display interface, for providing a dialog with a patient, including inquiring a patient's health status and receiving a response from the patient on the display interface;
a semantic analyzer, for extracting medical information of the patient based on the response from the patient, wherein the response from the patient is a first expression in a first expression category;
a medical knowledge database storing a second expression of a medical condition corresponding to the medical information, wherein the second expression is in a second expression category, wherein the second expression is obtained by a mapping apparatus implemented by a hardware circuit to map a term in the response from the patient into a corresponding express of the second expression; and
a report generator, for generating a medical condition inquiry report having the medical information with the second expression on the display interface;
wherein the mapping apparatus further comprises a term vector calculator for calculating a term vector of each term in a term set, wherein both a set of predetermined expressions of semantic knowledge and a set of terms in the response expression are proper subsets of the term set, and the term vector calculator is further configured to decompose a term-term matrix, at least partially map a term to a potential semantic space based on an Explicit Semantic Analysis (ESA) to obtain a vector of the term in the potential semantic space and take the vector as a term vector of the term; and
wherein the term vector calculator calculates the term vector of each term in the term set in a following manner:

$$M \approx P^T W \quad (3)$$

$$\min_{P,W} \sum_{i=1}^{n} \sum_{j=1}^{m} (M_{i,j} - P_i^T W_j)^2 + \quad (4)$$

$$\alpha \sum_{i=1}^{n} \sum_{j=1}^{n} E_{i,f} \|P_i - P_f\|_F^2 + \lambda(\|P\|_F^2 + \|W\|_F^2)$$

where $V=\{v1, v2, \ldots, vm\}$ represents the term set, $v_i$ and $v_j$ ($1 \le i, j \le m$) each represents a single term, $M \in R^{m \times m}$ represents the term-term matrix, $M_{i,j}$ is a Term Frequency-Inverse Document Frequency (tf–idf) weight of the term $v_j$ in the term $v_i$, $E_{i,j}$ is a similarity between the terms $v_i$ and $v_j$, $\|\bullet\|^2_F$ is a Frobenius norm, $\alpha$ and $\lambda$ are preset non-negative parameters, $P \in R^{k \times m}$, $W \in R^{k \times m}$, and R is a real number; and P is calculated under a condition in which the formula (4) is minimum according to the formula (3) and the formula (4), and a term vector $P_i$ of the term $v_i$ and a term vector $P_j$ of the term $v_j$ are obtained.

\* \* \* \* \*